United States Patent
Gatfield et al.

(10) Patent No.: US 7,776,923 B2
(45) Date of Patent: *Aug. 17, 2010

(54) USE OF TRANS-PELLITORIN AS FLAVOR SUBSTANCE

(75) Inventors: Ian Lucas Gatfield, Hoexter (DE);
Jakob Peter Ley, Holzminden (DE);
Gerhard Krammer, Holzminden (DE);
Heinz-Jurgen Bertram, Holzminden (DE); Ilse Loenneker, Bevern (DE);
Arnold Machinek, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 603 days.

This patent is subject to a terminal disclaimer.

(21) Appl. No.: 10/483,668

(22) PCT Filed: Nov. 13, 2003

(86) PCT No.: PCT/EP03/12686

§ 371 (c)(1),
(2), (4) Date: Jul. 27, 2004

(87) PCT Pub. No.: WO2004/043906

PCT Pub. Date: May 27, 2004

(65) Prior Publication Data

US 2004/0241312 A1    Dec. 2, 2004

(30) Foreign Application Priority Data

Nov. 14, 2002   (DE) ................................. 102 53 331

(51) Int. Cl.
*A01N 37/18*   (2006.01)
*A61K 31/16*   (2006.01)
(52) U.S. Cl. .................................................... 514/626
(58) Field of Classification Search .................. 426/650; 514/626

See application file for complete search history.

(56) References Cited

U.S. PATENT DOCUMENTS

| 4,088,788 A * | 5/1978 | Ream et al. ..................... 426/3 |
| 4,671,962 A * | 6/1987 | Leroux ....................... 426/51 |
| 2003/0039706 A1 | 2/2003 | Hirose et al. |
| 2003/0152682 A1 | 8/2003 | Ley et al. |

FOREIGN PATENT DOCUMENTS

| EP | 1 323 356 | 7/2003 |
| JP | 5683416 | 7/1981 |
| JP | 57075961 | 5/1982 |
| JP | 62175456 | 8/1987 |
| JP | 10265347 | 10/1998 |
| JP | 20000270810 | 10/2000 |

OTHER PUBLICATIONS

M. Jacobson: *Pellitorine Isomers. II The Synthesis of N-Isobutyl-trans-2, trans-4-decadienamide*, Journal of the American Chemical Society, vol. 75, 1953, pp. 2584-2586.
R. Gamboa-Leon, W.S. Chilton: *<Isobutylamide numbing agents of toothache grass, Ctenium aromaticum*, Biochemical Sytematics and Ecology, vol. 28, 2000, pp. 1019-1021.
Gulland, J.M., *Pellitorine, the pungent principle of Anacyclus pyrethrum*, Database Caplus Online, Chemical Abstracts Service, Columbus, OH, US, Database accession No. 1930:23787.
Chemical Abstracts, 1930, vol. 24, 2544a-d.

* cited by examiner

*Primary Examiner*—Yong S Chong
(74) *Attorney, Agent, or Firm*—Novak Druce+Quigg; Gregory A. Nelson; Gregory M. Lefkowitz

(57) ABSTRACT

The invention concerns the use of 2E,4E-decadienoic acid-N-isobutylamide (trans-pellitorin) as flavorant, in particular as salivation inducing flavor substance, preferably in a foodstuff or nutrient, an oral hygienic preparation or a gourmet or snack preparation. Further, the invention concerns preparations, semi-finished preparations as well as fragrance, aroma and taste compositions, containing trans-pelletorin as well as a processes for the production of trans-pelletorin.

5 Claims, No Drawings

USE OF TRANS-PELLITORIN AS FLAVOR SUBSTANCE

CROSS REFERENCE TO RELATED APPLICATION

This application is a national stage of PCT/EP03/12686 filed Nov. 13, 2003 and based upon DE 102 53 331.8 filed Nov. 14, 2002 under the International Convention.

BACKGROUND OF THE INVENTION

1. Field of the Invention

The invention concerns the use of 2E,4E-decadienoic acid-N-isobutylamide (trans-pelletorin) as flavor substance, in particular as salivation inducing flavor substance, preferred in foodstuff, oral hygiene or gourmet food preparations. The invention further concerns preparations, semi-finished products as well as fragrances, flavors and taste compositions containing trans-pelletorin, as well as a process for the production of trans-pelletorin.

2. Description of the Related Art

Salivation inducing substances are employed for example in order to combat clinical dry mouth, to awake the appetite or to improve oral hygiene, wherein due to the elevated flow of saliva harmful substances or germs are rinsed from the oral cavity. In foodstuff preparations usually tasteful acidic substances are employed, for example citric acids, vinegar or malic acid (as found in unripe apples). Special substances exciting the salivary glands such as for example pilocarpin extracted from the jaborandi tree are employed in clinical dry mouth (Acta Med. Croatica 2000, 54, 65-67). Such high potent cholinergic parasympathomimetics generally have serious side effects and are in part very poisonous.

Among a long chain fatty acid alkyl amides, 2E,6Z,8E-decatrienoic acid-N-isobutylamide (spilanthol) has been described as strongly salivation inducing and tingly or prickly. Spilanthol is however at the same time above all spicy-hot and strongly numbing as well as an astringent (Lebensm.-Wiss. U.-Technol. 1992, 25, 417-421). Other, longer chain polyenoic acid-N-isobutylamides or polyyne acid-N-isobutylamide appear to be more strongly salivation inducing, but however exhibit in addition a bitter taste sensation (see above citation).

SUMMARY OF THE INVENTION

It is the task of the present invention to develop a substance with a salivation inducing and/or prickly effect as well an otherwise substantially neutral flavor profile, which can be employed as flavor substance in preparations, in particular in foodstuffs, oral hygiene or gourmet preparations.

The invention thus concerns the employment of 2E,4E-decadienoic acid-N-isobutylamide (trans-pelletorin) as flavor substance, preferably as flavor substance with a salivation inducing and/or prickling or tingling effect, in particular preferred as flavor substances with salivation inducing and/or prickling effect in foodstuffs, oral hygiene and/or gourmet preparations.

The invention is further concerned with preparations, semi-finished (half-baked) preparations and fragrances, flavor and taste compositions, containing 2E,4E-decadienoic acid-N-isobutylamide, preferably containing synthetic 2E,4E-decadienoic acid-N-isobutylamide.

The inventive trans-pelletorin has been found in taste research to provide a pleasant saliva-inducing and slightly prickly sensory impression, with relatively prolonged effect. Surprisingly, a saliva inducing effect is only to be observed when the concentration lies below 20 ppm, in particular below 10 ppm in the final product, for example in a finished preparation. At such a time no additional sensory impressions can be detected, so that the taste profile is very neutral. The substantially neutral taste profile provides a substantial advantage for ability to incorporate into preparations, since the trans-pelletorin brings about no change or corruption of the taste profile of the preparation.

This is in particular surprising for the reason that J. Am. Chem. Soc. 1953, Volume 75, 2584-2586 describes during tasting of trans-pellitorins in the pure state, besides an elevated saliva flow, a strong burning effect on the tongue. Its sensory impression was also described as primarily numbing (J. Agric. Food Chem., 1981, Volume 29, pages 115 on or Fitoterapia, 2001, Volume 72, pages 197 on).

The natural occurrence of pure 2E,4E-decadienoic acid-N-isobutylamide has often been described in the literature; for example, it occurs in pepper (Übersicht G. M. Strunz, Stud. Nat. Prod. Chem. 2000, Volume 24 (Bioactive Natural Products (Part E)), 683-738).

Natural products, such as for example natural extracts, which contain trans-pellitorin, are characterized by additional taste effects and thus no neutral taste profile. This is frequently an undesired characteristic of natural products during their incorporation into preparations. For this reason the employment of synthesized, that is, synthetic trans-pellitorin, is preferred in the present invention.

In a particularly preferred embodiment of the invention 2E,4E-decadienoic acid-N-isobutylamide is employed in combination with other saliva inducing, prickly, spicy and/or warm tasting substances or plant extracts. In this manner it is possible to intentionally achieve a particularly well rounded sensory profile.

Other saliva inducing, prickly, spicy hot and/or warm tasting substances can be for example gourmet acids (for example citric acids, malic acids, vinegar acids), capsaicin, dihydrocapsaicin, gingerol, paradol, shogaol, piperin, carboxylic acid-N-vanillylamide, in particular nonanoic acid-N-vanillylamide, 2-alkenoic acid, in particular 2-nonenoic acid-N-isobutylamide, spilanthol, 2-nonenoic acid-N-4-hydroxy-3-methoxyphenylamide, alkylethers of 4-hydroxy-3-methoxybenzyl alchohol, in particular 4-hydroxy-3-methoxybenzyl-n-butylether, alkylether of 4-acyloxy-3-methoxybenzyl alchohol, in particular 4-acetyloxy-3-methoxybenzyl-n-butylether and 4-acetyloxy-3-methoxybenzyl-n-hexylether, alkylethers of 3-hydroxy-4-methoxybenzyl alchohol, alkylethers of 3,4-dimethoxybenzyl alchohols, alkylethers of 3-ethoxy-4-hydroxybenzyl alchohol, alkylethers of 3,4-methylenedioxybenzyl alchohol, (4-hydroxy-3-methoxyphenyl) acetic acid amide, in particular (4-hydroxy-3-methoxyphenyl) acetic acid-N-n-octylamide, ferulic acid phenethylamides, nicotinaldehyde, methylnicotinate, propylnicotinate, 2-butoxyethylnicotinate, benzylnicotinate, 1-acetoxychavicol, polygodial, isodrimeninol or pilocarpin.

The trans-pellitorin can preferably be used with at least one additional N-isobutylamide selected from the group consisting of decanoic acid, 2E-decenoic acids, 2E,4Z-decadienoic acids, 2Z,4E-decadienoic acids, 2Z,4Z-decadienoic acids, 2E,4Z,7Z-decatrieneoic acids, 3Z,5E-decadienoic acids or 3Z,5E,7Z-decatrienoic acids. Preferred is a mixture of at least 80 wt. % 2E,4E-decadienoic acid-N-isobutylamide and at most 20 wt. % 2E,4Z-decadienoic acid-N-isobutylamide.

Salivation inducing, prickly, spicy hot and/or warm tasting plant extracts can be any of the plant extracts suitable for foodstuffs or oral hygiene, which bring about a salivation inducing, prickly, spicy hot and/or warm sensory impression. Preferred as plant extracts are for example pepper extracts (*Piper* ssp., in particular *Piper nigrum*), water pepper extracts (*Polygonum* ssp., in particular *Polygonum hydropiper*), extracts of *Allium* ssp. (in particular onions and garlic extracts), extracts of radish (*Raphanus* ssp.), horseradish extracts (*Cochlearia armoracia*), extracts of black (*Brassica nigra*), wild or yellow mustard (*Sinapis* ssp., in particular *Sinapis arvensis* and *Sinapis alba*), pyrethrum extracts (*Ancyclus* ssp., in particular *Anacylcus pyrethrum* L.), purple cone flower extracts (*Echinaceae* ssp.), extracts of Szechuan-pepper (*Zanthoxylum* ssp., in particular *Zanthoxylum piperitum*), spilanthes extract (*Spilanthes* ssp., in particular *Spilanthes acmella*), chili extract (*Capsicum* ssp., in particular *Capsicum frutescens*), paradise corn or grain extract (*Aframomum* ssp., in particular *Aframomum melegueta*[Rose] K. Schum.), ginger extract (*Zingiber* ssp., in particular *Zingiber officinale*), galangal extract (*Kaempferia galanga* or *Alpinia galanga*) and jaborandi extract (*Pilocarpus-Spezies*, in particular *Pilocarpus jaborandi*).

The inventive plant extracts can be obtained from the corresponding fresh or dried plants or plant parts, in particular however from white, green or black pepper corns, water pepper corns, onions and garlic, radish roots, horseradish, mustard seeds, purple cone flower roots, Bertram roots, pyrethrum roots, plant parts from *Zanthoxylum*-varieties, plant parts from spilanthes-varieties, chili pods, paradise corns or ginger or galangal roots as well as jaborandi. Conventionally the dried plant parts, which are preferably cut into small pieces in advance, are extracted with a solvent suitable for foodstuffs and gourmet substances, preferably ethanol, water, hexane or heptane or ethanol/water mixtures, at 0° C. up to the boiling point of the respective solvent or solvent mixture, subsequently filtered, and the filtrate is wholly or partially reduced, preferably by distillation, freezing or spray drying. The thus obtained raw extract can be further processed, for example treated with steam, usually at a pressure of 0.01 mbar up to atmospheric pressure, and/or taken up in a solvent suitable for foodstuffs and gourmet substances.

A solvent suitable for foodstuffs and gourmet substances can be for example: water, ethanol, methanol, propylenglycol, glycerin, acetone, dichlormethane, acetic acid ethylester, diethylether, hexane, heptane, triacetine, plant oils or fats, as well as supercritical carbon dioxide or mixtures of the above-mentioned solvents.

The methods for synthesizing trans-pellitorin described in the state of the art literature involve multiple stages and produce poor yields (J. Am. Chem. Soc. 1953, volume 75, 2584-2586) or employ toxic reagents such as for example the toxic selenium dioxide (Bull. Chem. Soc. Jpn., 1984, volume 57, pages 3013 on).

The invention is thus further concerned with a process for production of 2E,4E-decadienoic acid-N-isobutylamide, thereby characterized, that a) a 2E,4E- or 2E,4Z-decadienoic acid ester or a mixture of this ester with isobutylamine is transformed or converted in the presence of a catalyst and b) the product formed in step a), in certain cases following purification steps, is isomerized to 2E,4E-decadienoic acid-N-isobutylamide;

or i) a 2E,4Z-decadienoic acid ester or a mixture of 2E,4E- and 2E,4Z-decadienoic acid ester is isomerized to 2E,4E-decadienoic acid ester and ii) the product formed in step i), in certain cases following purification steps, is converted with isobuylamine in the presence of a catalyst.

Of course step i) can be omitted and one could substitute directly a 2E,4E-decadienoic acid ester in the conversation with isobutylamine.

Preferred is a process wherein the conversation with isobutylamine occurs in the presence of a catalyst, preferably an enzyme, in particular an enzyme with lipase activity, wherein the enzyme can be a free protein or be present in association with a carrier, one subjects the resulting reaction mixture with non-converted 2,4-decadienoic acid ester, in certain cases with saponification, preferably with an enzyme in an aqueous medium or a base diluted with water, in particular preferably an aqueous solution of inorganic basic salts, the formed 2,4-decadienoic acids are separated, preferably extractively, the purified or unpurified raw product is isomerized to 2E,4E-decadienoic acid-N-isobutylamide and subsequently the mixture is purified with physico-chemical methods, preferably by crystallization, chromatography, distillation or co-distillation.

The process can be explained on the basis of the following formula equation:

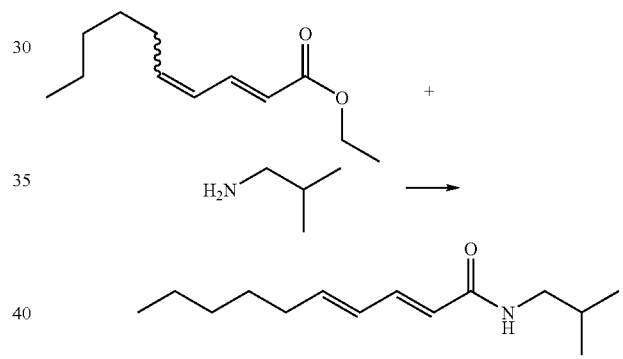

It was surprisingly determined that the inventive process makes possible a very simple obtaining of high yield and easy to purify amounts of the desired 2E,4E-decadienoic acid-N-isobutylamide. Besides this, it becomes possible with the employment of natural reagents, in the sense of the governmental flavor substance regulations, to obtain natural trans-pellitorin.

Among the 2E,4E- or 2E,4Z-decadienoic acid esters, these are preferably esters of the 2E,4E- or 2E,4Z-decadienoic acid with aliphatic monohydric alcohols with 1 to 20 carbon atoms, in particular however methanol, ethanol, 1-propanol, 2-propanol, 1-butanol, 2-butanol, 2-methyl-1-propanol, 2-methyl-2-propanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol or multi-hydric alcohols with 2 to 18 carbon atoms such as ethylene glycol, 1,2-propylene glycol, 1,3-propylene glycol, glycerin, pentaerythritol, sugar alcohols such as erythritol, sorbitol, glucitol, mannitol, monosaccharides such as tetroses, for example erythrose or threose, pentoses, for example arabinose, ribose, lyxose, xylose, hexoses such as allose, altrose, galactose, mannose, gulose, idose, glucose, talose, fructose, oligosaccharide such as maltose, raffinose, sucrose, maltooligosaccharides or lactoses, wherein further OH-groups of the multi-hydric alcohols can be esterified with aliphatic, saturated or unsaturated carboxcyclic acids, as well as their mixed or saturated or unsaturated hydroxycarboxcyclic acids with 4 to 20 carbon atoms, which for their part can be esterified with the above-mentioned alcohols.

Preferred aliphatic saturated or unsaturated carboxcyclic acids in the sense of the invention are saturated or mono- or multiple unsaturated linear carboxylic acids with 2 to 26 carbon atoms, in particular however acetic acid, propionic acid butyric acid, pentanoic acid, hexonic acid, hexanoic acid, octanoic acid, nonanoic acid, 2E-nonoic acid, decanoic acid, 2E-decenoic acid, the various isomers of decadiene- or decatrieneoic acid, for example 2E,4E-decadieneoic acid, 2E,4Z-decadieneonic acid, 2E,4Z,7Z-decatrieneonic acid, 3Z,5E-decadieneonic acid, 3Z,5E,7Z-decatrieneonic acid, deca-2,8-dien-4,6-diinonic acid, deca-2-en-4,6,8-triineonic acid, undecanoic acid, dodecanonic acid, tridecanonic acid, tetradecanonic acid, pentadecanonic acid, hexadecanonic acid, 9E- or 9Z-hexadecenonic acid, heptadecanonic acid, octadecanonic acid, 9E- or 9Z- or 11E- or 11Z-octadecenonic acid, the various geometric isomers of 9,12-octadecadienonic acid, the 6,9,12-octadecatrienonic acids, the 9,12,15-octadecatrienonic acids, the 6,9,12,15-octadecatetraenonic acids, the nonadecanonic acids, the eicosanonic acids, the various geometric isomers of eicosaenoic acids, the 11,14-eicosadienoic acids, the 8,11,14-eicosatrienoic acids, the 5,8,11,14-eicosatetraenoic acids, the 5,8,11,14,17-eicosapentaenoic acids, the 10,13,16-docosatrienoic acids, the 7,10,13,16-docosatetraenoic acids, the 4,7,10,13,16-docosapen-taenoic acids and the 4,7,10,13,16,19-docosahexaenoic acids.

The 2,4-decadienoic acids esters in the sense of the invention are preferably in the form of natural or concentrated processed triglycerides, for example from stillingia (tallow-seed) oil or as methyl- or ethyl esters. Particularly preferred is a fraction obtained by enzymatic conversion of stillingia oil in ethanol and subsequent distillation, thereby characterized, that it contains at least 80 wt. % ethyl 2E,4Z-decadienoate.

Isomerization in the sense of the invention means that the other remaining possible geometric isomers of 2,4-decadienoic acid or (2E,4Z-, 2Z,4Z- or 2Z,4E-) not corresponding to the trans-pellitorin are converted to 2E,4E-isomers by known methods. Preferably the 2E,4Z-isomer is converted to the 2E,4E-isomer by treatment with iodine or by radiation with UV-light (wavelength between 250 and 320 nm). The isomerization can be carried out to the 2,4-decadienoic acid-N-isobutylamides or the 2,4-decadienoic acid esters.

Further subject of the invention is the nutritive or taste experience enhancing preparation containing 2E,4E-decadienoic acid-N-isobutylamide in an effective amount and in certain cases other conventional bases, enhancers and supplements or additives for nutritive and pleasure substances. The preparations contain in general 0.000001 wt. % (0.01 ppm) to 0.05 wt. % (500 ppm), preferably 0.00001 wt. % (0.1 ppm) to 0.005 wt. % (50 ppm), particularly preferably 0.00001 wt. % (0.1 ppm) to 0.0015 wt. % (15 ppm), of 2E,4E-decadienoic acid-N-iso-butylamide, based on the total weight of the preparation. Further, conventional base, enhancers and additives for nutrient or enjoyment substances can be contained in amounts of 0.000001 to 99.999999 wt. %, preferably 10 to 80 wt. %, measured based on the total weight of the preparation. Further, the preparations can container water in amounts of up to 99.999999 wt. %, preferably 5 to 80 wt. %, based on the total weight of the preparation.

The nutrition or the enjoyment enhancing preparations in the sense of the invention include for example baked goods (for example bread, dry crackers, cake, other baked goods) sweets (for example chocolate, fruit gelatin candy, hard and soft caramel, chewing gum), alcoholic or non-alcoholic drinks (for example coffee, tea, wine, wine containing drinks, beer, beer containing drinks, liquors, whiskeys, brandies, fruit containing lemonade, isotonic drinks, refreshing drinks, nectars, fruit and vegetable juices, fruit or vegetable juice preparations), instant drinks, meat products (for example ham, fresh sausage or raw sausage preparations), eggs or egg products (dry eggs, egg white, egg yellow), grain or cereal products (for example breakfast cereals, muesli bars), milk products (for example milk drinks, ice cream, yogurt, kefir, fresh cheese, soft cheese, hard cheese, dry milk powder, whey, butter, buttermilk), fruit preparations (for example jams, fruit ice cream, fruit sauces), vegetable preparations (for example ketchup, sauces, dry vegetables), snack articles (for example baked or fried potato chips or potato dough products, extradites based on corn or peanut), products based on fat or oil or emulsions thereof (for example mayonnaise, remoulade dressings (salad dressings)), finished preparations and soups, herbs, herb mixtures as well as in particular sprinkling herbs (seasonings), which have application in the field of snacks. The preparations in the sense of the invention can also serve in preparations which are semi-finished (partially cooked or baked) products for production of further products for nutrition or luxury foods. The preparations in the sense of the invention can also be provided in the form of capsules, tablets (not coated as well as coated tablets, for example gastric juice resistant coatings), pills, granulates, pellets, solid mixtures, dispersions in liquid phases, as emulsions, as powders, as solutions, as paste or other swallowable or chewable preparations as nutritional supplements.

A particular preferred embodiment of the invention concerns preparations for enhancing oral hygiene, in particular tooth care substances such as dental pastes, dental gels, dental powders, mouth wash, chewing gum and other oral care substances, containing 2E,4E-decadienoic acid-N-isobutylamide in an effective amount and in certain cases other conventional bases, supplements and additives for such preparations. They contain as a rule 0.000001 wt. % (0.01 ppm) to 0.05 wt. % (500 ppm), preferably 0.00001 wt. % (0.1 ppm) to 0.005 wt. % (50 ppm), particularly preferably 0.00001 wt. % (0.1 ppm) to 0.0015 wt. % (15 ppm), based upon the total weight of the preparation, of 2E,4E-decadienoic acid-N-isobutylamide. Further conventional bases, supplements and additives for the oral hygiene preparation can be contained in amounts of 0.000001 to 99.999999 wt. %, preferably 10 to 80 wt. %, based upon the total weight of the preparation. Further, the preparations can contain water in amounts of up to 99.999999 wt. %, preferably 5 to 80 wt. %, based on the total weight of the preparation.

Dental care compositions containing 2E,4E-decadienoic acid-N-isobutylamide, are comprised in general of an abrasive system (friction or polishing agent), such as for example silicic acids, calcium carbonates, calcium phosphates, aluminum oxides and/or hydroxy apatites, of surface active substances such as for example sodium lauryl sulfate, sodium lauryl sarcosinate, and/or cocamidopropylbetaine, of moisturizers such as glycerine and/or sorbitol, of thickeners such as carboxymethylcellulose, polyethylene glycols, carrageenans and/or Laponites®, of sweeteners such as saccharin, of stablizers and of active substances such as sodium fluoride, sodium monofluorphosphate, stannous fluoride, quarternary ammonium fluorides, zinc citrate, zinc sulfate, zinc pyrophosphate, zinc dichloride, mixtures of various pyrophosphates, triclosan, cetylpyridiniumchloride, aluminiumlactate, calcium citrate, calcium nitrate, calcium chloride, strontium chloride, hydrogen peroxide, aromas and/or sodium bicarbonate.

Chewing gums containing 2E,4E-decadienoic acid-N-isobutylamide are comprised in general of a chewing gum base, that is, a chewing mass which does not become plastic upon chewing, of sugars of various types, sugar exchange substances, sweeteners, sugar alcohols, moisturizers, thickeners, emulsifiers, aromas and stablizers.

The inventive preparations can also preferably be employed as sprinkle herbs, so-called seasonings, in order to minimize the dry mouth feel which occurs when eating corn-, potato- or rice-flour chips and snacks, and to improve the sensory total impression.

Suitable seasonings include for example synthetic, natural or natural like flavorants as well as carrier substances such as maltodextrine, salts such as cooking salt, seasonings such as paprika and pepper, sweeteners such as saccharin, and taste enhancers or amplifiers such as monosodiumglutamate and/or inosinmonophosphate.

The inventive preparations containing 2E,4E-decadienoic acid-N-isobutylamide can be produced in such a state that 2E,4E-decadienoic acid-N-isobutylamide is incorporated as a substance or as a solution of in the form of a mixture with a solid or liquid carrier substances into the food stuff, the oral hygiene or the gourmet preparation. Preferably, the inventive preparation in the form of a solution containing 2E,4E-decadienoic acid-N-isobutylamide can also be converted to a solid preparation by spray drying.

For producing the preparations, it is possible in a further preferred embodiment that the 2E,4E-decadienoic acid-N-isobutylamide and in certain cases other components of the inventive preparation also first be incorporated into emulsions, into liposomes, for example beginning with phosphatidylcholine, into microspheres, into nanospheres or also into capsules of a matrix suitable for consumables and snack foods, for example of starch, starch derivatives, other polysaccharides, natural fats, natural waxes or of proteins, for example gelatine. A further embodiment is comprised therein, that 2E,4E-decadienoic acid-N-isobutylamide is complexed first with suitable complexing agents, for example with cyclodextrin or cyclodextrin derivatives, preferably cyclodextrin, and employed in this form.

As other components of the inventive preparation for foodstuffs or enjoyment enhancing preparations, enhancers and additives for foodstuffs or enjoyment enhancing preparations can be employed, for example water, mixtures of fresh or processed, plant or animal based or raw substances (for example raw, baked, dried, fermented, smoked and/or dried meat, egg, bone, cartilage, fish, crustaceans and shell fish, vegetables, fruits, herbs, nuts, vegetable or fruit juices or pastes or mixtures thereof), digestible or also non-digestible carbohydrates (for example sugar, maltose, fructose, glucose, dextrine, amylose, amylopectin, inulin, xylan, cellulose), sugar alcohols (for example sorbitol, mannitol, xylitol), natural or hardened or saturated fats (for example tallow, lard, palm fat, coco fat, hardened plant fat), fatty oils (for example sunflower oil, peanut oil, corn oil, thistle oil, olive oil, walnut oil, fish oil, soy oil, sesame oil), fatty acids or their salts (for example calcium stearate, calcium palmitate), proteinogenic or non-proteinogenic amino acids and related compounds (for example taurine, kreatine, kreatinine), peptides, natural or processed proteins (for example gelatin), enzymes (for example peptidases, glucosidases, lipases), nucleic acids, nucleotides (inositolphosphate), flavor modifier substances (for example sodium glutamate, 2-phenoxypropionic acid), emulsifiers (for example lecithin, diacylglycerol), stabilizers (for example carageenan, alginate, carob seed flour, guar gum), conservatives (for example benzoic acid, sorbic acid), antioxidants (for example tocopherol, ascorbic acid), chelators (for example citric acids), organic or inorganic acids (for example malic acid, acetic acid, citric acid, tartaric acid, phosphoric acid), bitter substances (for example chinin, caffeine, limonene), sweeteners (for example saccharin, cyclamate, aspartam, neotame, neohesperidindihydrochalcone), mineral salts (for example sodium chloride, calcium chloride, magnesium chloride, sodium phosphate), substances for preventing enzymatic browning (for example sulfate, ascorbic acid), etheric oils, plant extracts, natural or synthetic colorants or color pigments (for example carotinoids, flavonoids, anthocyane, chlorophylls and their derivates), herbs as well as aromatic substances, synthetic natural or natural like flavors and taste substances.

Preferably the inventive preparation can also contain a flavor composition in order to round out or enhance the taste and/or fragrance of the preparation. Suitable aromatic compositions contain for example synthetic, natural or identical to natural aromatic substances as well as fragrance substances, in particular however also other salivation inducing, prickly, hot, spicy or warm tasting substances or plant extracts.

It is further within the scope of the invention to use the inventive preparations as semi-ready or semi-baked goods, for the flavor enhancement of the finished goods prepared therefrom.

Further within the scope of the invention are fragrance, aroma and taste substance compositions, containing 2E,4E-decadienoic acid-N-isobutylamide. These compositions contain in general 0.001 wt. % to 5 wt. %, preferably 0.01 wt. % to 2 wt. %, particularly preferably 0.05 wt. % to 1 wt. % of 2E,4E-decadienoic acid-N-isobutylamide, based upon the total weight of the composition.

The invention can be described in greater detail on the basis of the following examples.

EXAMPLES

Example 1

2E,4E-decadienoic acid-N-isobutylamide (Trans-Pellitorin) by Enzymatic Conversion with ethyl-2E,4Z-decadienoate with Subsequent Isomerization Conversion with Isobutylamine:

10 g ethyl-2E,4Z-decadienoate, 4.7 g Chirazym L-2 (c.-f., C2, lyo., Catalog-No. 1859242, Roche Diagnostics, Basel, Switzerland) and 4 g isobutylamine were stirred 4 days at 55° C. 100 ml diethylether were added to the preparation which was then filtered; the filtrate was evaporated in vacuum (raw yield 15.2 g). The product was stirred into a 10% KOH/methanol (1:1-mixture) for 45 min at room temperature, extracted with ether, the etheric phase was dried over sodium sulphate, filtered and the filtrate was evaporated. The raw intermediate product was chromatrographed on silica gel 60 (eluent hexane/ethylacetate 10:1 (v/v)). Yield 9.1 g (GC: 99.4%).

$^1$H-NMR (CDCl$_3$; 200 MHz): δ=7.56 (1H, ddd, 11.5 Hz, 14.9 Hz, 1.0 Hz), 6.08 (1H, dddd 11.5 Hz, 10.8 Hz, 1.4 Hz, 0.6 Hz), 5.82 (1H, d, 14.9 Hz), 5.79 (1H, dtd 10.8 Hz, 7.8 Hz, 0.9 Hz), 5.50 (1H, bs), 3.18 (2H, dd, 6.8 Hz, 6.1 Hz), 2.36-2.22 (2H, m), 1.81 (1H, m, 6.7 Hz), 1.50-1.22 (6H, m), 0.93 (6H, d, 6.7 Hz), 0.88 (3H, m) ppm.

$^{13}$C-NMR (CDCl$_3$; 50 MHz): δ=166.34 (C), 140.07 (CH), 135.76 (CH), 126.28 (CH), 123.78 (CH), 46.96 (CH$_2$), 31.41 (CH$_2$), 29.14 (CH$_2$), 28.63 (CH), 28.15 (CH$_2$), 22.52 (CH$_2$), 20.15 (CH$_3$), 14.02 (CH$_3$) ppm.

Isomerization:

277 mg of the purified 2E,4Z-decadienoic acid-N-isobutylamide was stirred with 29 mg iodine in 10 ml toluol for one hour at room temperature. The mixture was chromatographically separated on silica gel 60 with hexane/ethylacetate 5:1 (v/v) as eluates. Yield: 61 mg (purity >95%, NMR).

$^1$H-NMR (CDCl$_3$; 200 MHz): δ=7.19 (1H, dd, 14.9 Hz, 9.7 Hz), 6.13 (1H, dd 15.1 Hz, 9.6 Hz), 6.07 (1H, dd, 15.1 Hz, 6.4 Hz), 5.75 (1H, d 14.9 Hz), 5.50 (1H, bs), 3.17 (2H, dd, 6.9 Hz, 6.1 Hz), 2.14 (2H, dd, 7 Hz, 6.4 Hz), 1.80 (1H, m, 6.7 Hz), 1.42 (2H, m, 7.1 Hz), 1.37-1.22 (4H, m), 0.93 (6H, d, 6.7 Hz), 0.89 (3H, m) ppm.

Isomerization Variant 1:

To 3.1 g of the raw intermediate product from the conversion with isobutylamine was added 60 mg iodine in 20 ml toluol, and this was stirred 26 h at room temperature. 30 ml n-hexane were added and the mixture was stored at 18° C. 1 h. The crystalline product was filtered off (GC: 86% 2E,4E-isomer, 10.5% 2E,4Z-isomer). By recrystallization out of approximately 30 ml n-hexane it was possible to obtain a 95% (pure) product (Yield 1.6 g).

Isomerization Variant 2:

3.1 g of the raw intermediate product obtained from the conversion with isobutylamine were dissolved in 100 ml ethanol and while keeping cold were irradiated with a mercury vapor high pressure lamp with quartz glass tube for 8 hours. The solution was vaporized and the oily residue (GC: 22% 2E,4E-isomer, 62% 2E,4Z-isomer) was chromatographically purified (Yield approximately 400 mg).

Example 2

Tasting

The trans-pellitorin was dissolved in ethanol and the ethanolic solution was then diluted with an 11 wt. % sugar solution (final concentration: c). For tasting, respectively approximately 5 ml of the sugar solution was respectively swallowed. A group of 6 to 8 testers had tasted the solution:

c=10 ppm: salivation inducing, slightly prickly, not spicy hot c=20 ppm: salivation inducing, slightly numbing, slightly fatty, weakly fruity, prickly, persistent, not spicy hot

Example 3

Use in a Toothpaste

| Part | Ingredient | Content in wt. % |
|---|---|---|
| A | Demineralized water | 22.00 |
|   | Sorbitol (70%) | 45.00 |
|   | Solbrol ® M, sodium salt (Bayer AG, p-Hydroxybenzoic acid alkylester) | 0.15 |
|   | Trisodiumphosphate | 0.10 |
|   | Saccharin, 450 fold | 0.20 |
|   | Sodiummonofluorphosphate | 1.12 |
|   | Polyethylenglycol 1500 | 5.00 |
| B | Sident 9 (abrasive Siliconedioxide) | 10.00 |
|   | Sident 22 S (thickened silicondioxide) | 8.00 |

-continued

| Part | Ingredient | Content in wt. % |
|---|---|---|
|   | Sodiumcarboxymethylcellulose | 0.90 |
|   | Titaniumdioxide | 0.50 |
| C | Demineralized water | 4.53 |
|   | Sodiumlaurylsulfate | 1.50 |
| D | Taste Composition, containing 0.1 wt. % 2E,4E-decadienoic acid-N-isobutylamide | 1 |

The contents of Components A and B were respectively premixed and then mixed together well under vacuum at 25-30° C. for 30 min. Part C was premixed and added to A and B; D was added to this and the mixture was well stirred under vacuum at 25-30° C. for 30 min. After relaxing, the toothpaste was finished and can be filled.

Example 4

Use in a Sugarfree Chewing Gum

| Part | Ingredient | Content in wt. % |
|---|---|---|
| A | Chewing gum base, Company "Jagum T" | 30.00 |
| B | Sorbitol, powdered | 39.00 |
|   | Isomalt ® (Palatinit GmbH) | 9.50 |
|   | Xylitol | 2.00 |
|   | Mannitol | 3.00 |
|   | Aspartam ® | 0.10 |
|   | Acesulfam ® K | 0.10 |
|   | Emulgum ® (Colloides Naturels, Inc.) | 0.30 |
| C | Sorbitol, 70% | 14.00 |
|   | Glycerin | 1.00 |
| D | Flavor composition, containing 0.1 wt. % 2E,4E-decadienoic acid-N-isobutylamide | 1 |

Parts A through D were mixed and intensively kneaded. The raw material was then processed into ready to eat chewing gum in the shape of thin strips.

Example 5

Use in a Mouth Wash

| Part | Ingredients | Content (wt. %) |
|---|---|---|
| A | Ethanol | 10.00 |
|   | Cremophor ® CO 40 (BASF, Detergent) | 1.00 |
|   | Benzoic acid | 0.12 |
|   | Flavorant, containing 0.4 wt. % 2E,4E-decadienoic acid-N-isobutylamide | 0.25 |
| B | Demineralized water | 83.46 |
|   | Sorbitol, 70% | 5.00 |
|   | Sodium saccharine 450 | 0.07 |
|   | L-Blue 5000 e.c., 1 wt. % in water (colorant) | 0.10 |

Example 6

Use in a Seasoning for Deep Fried Snack Food 100 g of unseasoned tortilla chips were sprinkled with a mixture of 7 g cheese dry flavor for snacks and 0.07 g 2E,4E-decadienoic acid-N-isobutylamide.

Example 7

Use in a Cracker Cream Filling 100 g standard crème filling were intensively mixed with 0.4 g strawberry flavor and und 0.1 g 2E,4E-decadienoic acid-N-isobutylamide.

The invention claimed is:

1. A method for imparting a salivation inducing effect to a foodstuff preparation, an oral hygiene preparation or a gourmet or snack preparation, the method comprising:

adding to said preparation 2E,4E-decadienoic acid isobutylamide (trans-pellitorin) such that the concentration of trans-pellitorin in said preparation is 20 ppm or less, said trans-pellitorin being present in an amount sufficient to induce salivation and insufficient to produce a spicy hot sensation.

2. A method according to claim 1, wherein the trans-pellitorin is added in an amount of 0.01 to 10 ppm, based upon the finished preparation.

3. A method according to claim 1, wherein said trans-pellitorin is a synthetic trans-pellitorin.

4. The method according to claim 1, wherein the total amount of trans-pellitorin added to said preparation is sufficient to induce salivation and insufficient to produce a spicy hot sensation.

5. The method according to claim 1, further comprising adding to said preparation 2E,4Z-decadienoic acid-N-isobutylamide, said trans-pellitorin and said 2E,4Z-decadienoic acid-N-isobutylamide forming a mixture, wherein trans-pellitorin comprises at least 80 wt-% of said mixture.

* * * * *